(12) United States Patent
Chuang (10) Patent No.: US 6,601,440 B1
(45) Date of Patent: Aug. 5, 2003

(54) APPARATUS FOR DETECTING SATURATION OF WATER IN SOIL

(75) Inventor: Hsu-Chen Chuang, Shin-Dian (TW)

(73) Assignee: Taiwan Water & Soil Instrumentation, Inc., Taiwan (CN)

( * ) Notice: Subject to any disclaimer, the term of this patent is extended or adjusted under 35 U.S.C. 154(b) by 0 days.

(21) Appl. No.: 10/117,758

(22) Filed: Apr. 5, 2002

(51) Int. Cl.⁷ .................................................. G01N 1/00
(52) U.S. Cl. ........................................................ 73/73
(58) Field of Search ............................. 73/73, 306–308, 73/304 R, 313, 314, 864.74, 863.23; 340/624; 324/694, 696

(56) References Cited

U.S. PATENT DOCUMENTS

| | | | | |
|---|---|---|---|---|
| 3,646,293 A | * | 2/1972 | Howard | .................... 200/84 C |
| 4,445,788 A | * | 5/1984 | Twersky et al. | ............ 374/142 |
| 4,807,707 A | * | 2/1989 | Handley et al. | ............... 175/20 |
| 6,202,479 B1 | * | 3/2001 | Frybarger | ....................... 73/73 |

* cited by examiner

Primary Examiner—Robert Raevis
(74) Attorney, Agent, or Firm—Connolly Bove Lodge & Hutz LLP (57) ABSTRACT

An apparatus for detecting saturation of water in soil includes a housing including a lower section adapted for insertion in soil, a filter for permitting water into the housing while blocking soil, a sensor unit received in the housing for sending a signal when water level reaches a pre-determined position, and a control unit for receiving the signal from the sensor unit and for processing the signal.

14 Claims, 7 Drawing Sheets

APPARATUS FOR DETECTING SATURATION OF WATER IN SOIL

BACKGROUND OF INVENTION

1. Field of Invention

The present invention is directed to an apparatus for detecting saturation of water in soil.

2. Prior Art

In the field, when it rains, water enters soil. When water content in soil reaches saturation, soil tends to liquidate and collapse, thus causing landslide that could claim precious lives and properties. People have been working hard to prevent landslide. However, landslide occurs as a result of disastrous development of land in some cases, or is simply in God's hands in some other cases. For whatever cause it may be, landslide is not something that we can completely prevent. Yet, we hope that we can minimize loss of precious lives and properties by evacuation of people and their properties before landslide happens. To this end, people need a warning system.

Warning of landslide may be done by evaluation. Such evaluation is based on precipitation instead of water content in soil, since water content in soil is related to how big and how long the rain falls in an un-sheltered area. When and in what scale landslide may happen is predicted via calculation of precipitation. Such evaluation is simple, however it cannot predict precisely since it does not take into account factors related to terrain and geography.

In fact, landslide is more directly related to water content in soil than to precipitation. Saturation of water in soil can be deemed an omen of landslide, and accuracy for warning of landslide can be improved if apparatuses can be installed to monitor water contents in soil in various positions.

U.S. Pat. No. 4,801,865 discloses a moisture sensor for sensing water content in soil. It provides a reading that varies as water content in soil varies. The reading and the water content are in a linear relation when the water content is in a range of 50–90% of saturation. However, the reading stops changing linearly with respect to the water content soon after the water content rises over 90% of saturation. In fact, the reading almost comes to a complete stop after the water content rises over 99% of saturation. In this phase, it is difficult to know if the water content really stops rising or continues to rise. This does not cause any serious problem when the moisture sensor is used for irrigation, because it does not matter to stop watering a little bit sooner or later than 100% of saturation. However, this can cause a serious problem if the moisture sensor is used for warning of landslide, for both pre-mature warning and late warning are not desirable.

U.S. Pat. No. 4,959,639 teaches a device for detecting a fluid. Such a device includes a rod, a sleeve and a spring. The rod is inserted in the sleeve, and they are dimensioned so as to allow longitudinal movement relative to each other. A bottom end of the rod is affixed with the bottom end of the sleeve. A spring is also received in the sleeve. A top end of the spring is affixed with a top end of the sleeve while a bottom end of the spring abuts a top end of the rod. Thus, the sleeve is always loaded with tension. The sleeve is made of a material that loses its tensile strength when exposed to the liquid, thus allowing longitudinal movement of the top end thereof relative to the top end of the rod. A detection member is used to detect such a relative movement. Such a device can monitor presence of water; however, it cannot be used as a warning device for landslide for failing to distinguish the status of having some water from the status of saturation reached.

U.S. Pat. No. 4,531,087 discloses a sensor for monitoring moisture in soil by measuring conductivity between electrodes. In such a sensor, two electrodes are spaced apart and packed in a porous medium, protected by a filter medium that excludes particulates but passes moisture. The conductivity of the porous medium between the electrodes is measured to reflect water content in the porous medium. The conductivity is not a strictly linear function of water content in soil. Still, properly interpreted, it can provide valuable information regarding water content at some depth in soil. Simplistically stated, when the porous region is completely dry, there is no or minimal conductivity. A very low or no meter reading will result if current is measured. When the sensor is fully wetted, the conductivity will be at a maximum, and there will be a higher meter reading. To be economically practical, a sensor must work well in a wide variety of soils and be responsive to a wide variety of waters. However, no matter how wet the sensor would be with distilled water, for example, there would always be a low or no reading because conductivity of such water is very low. In dealing with some sorts of liquid, such a sensor may not work at all. Even it works in other sorts of liquid, it cannot distinguish the status of having water from the status of saturation reached since the conductivity does not vary sharply together with water content in soil. Therefore, such a sensor cannot be used as a good device for warning of landslide.

U.S. Pat. No. 5,179,347 discloses a sensor for sensing moisture in soil. Such a sensor includes a metal housing with a wall defining an internal cavity. A number of apertures are defined through the wall. A porous filter liner is received in the cavity, thus lining the wall. A granular transfer matrix with silica sand is received in the linear. A buffer tablet of compacted gypsum abuts the transfer matrix. An electrode matrix including silica sand abuts the buffer tablet. Two electrodes contact the electrode matrix. The electrodes are spaced apart from each other, and are bridged by the electrode matrix. A lead extends from each of the electrodes. The sensor is closed against entry of moisture from soil in contact therewith except through the apertures that allow the moisture to penetrate the liner and the transfer matrix and pass through the tablet. The moisture dissolves some electrolyte as it penetrates. The moisture further enters the electrode matrix so as to form an electrically conductive path between the electrodes. The conductivity or lack of conductivity of the electrode matrix between the electrodes is indicative of the presence or absence of moisture in the soil. Such a sensor can be used to monitor water content in soil. However, it cannot distinguish the status of having water from the status of saturation reached since the conductivity does not vary sharply together with water content in soil. Moreover, the buffer tablet will be consumed after such a sensor is used for some time, and then cannot work in some sorts of liquid. Such a sensor therefore cannot be used as a good device for warning of landslide.

U.S. Pat. No. 5,969,620 discloses a moisture monitor including a housing, an upper electrode, a lower electrode and a common electrode. The electrodes are all attached to the housing. In use, the housing is inserted in the ground or immersed in the water. As discussed in relation to Table 2, when none of the upper and lower electrodes contacts water, no alarm is provided, for assuming that the moisture monitor is not in use. When the upper and lower electrodes both contact water, no alarm is provided for interpreting that water level is high enough. Only when the lower electrode contacts water while the upper electrode does not, an alarm is provided for interpreting that the moisture is in use and water level is too low. Such a moisture obviously cannot be used to warn of landslide for it is designed to provide an alarm only when water level is too low, not too high.

Therefore, the present invention is intended to obviate or at least alleviate the problems encountered in the prior art.

SUMMARY OF INVENTION

It is an objective of the present invention to provide an apparatus for precisely detecting saturation of water in soil.

It is another objective of the present invention to provide a durable, accurate apparatus for detecting saturation of water in soil.

To achieve the above-mentioned and other objectives, there is provided an apparatus for detecting saturation of water in soil including a housing including a lower section adapted for insertion in soil, means for permitting water into the housing while blocking soil, a sensor unit received in the housing for sending a signal when water level reaches a pre-determined position, and a control unit for receiving the signal from the sensor unit and for processing the signal.

In another aspect of the present invention, an apparatus for detecting saturation of water in soil includes a housing including a lower section adapted for insertion in soil. A filter is used to permit water into the housing while blocking soil. A sensor unit includes lower and upper reed switches received in the housing, a float for floating on the water in the housing, thus performing as an indicator of the water level, and a magnet attached to the float so that the lower reed switch can detect the magnet and send a signal and that the upper reed switch can detect the magnet and send a signal. A control unit is used to receive the signals from the reed switches, and to divide the distance between the reed switches by the time difference between the signals so as to determine a rate of rising of the water level, and to provide an alarm if the rate reaches a pre-determined value.

BRIEF DESCRIPTION OF DRAWINGS

The present invention will be described in detail through illustration of some embodiments shown in the attached drawings wherein.

DETAILED DESCRIPTION OF EMBODIMENTS

Figure 1:
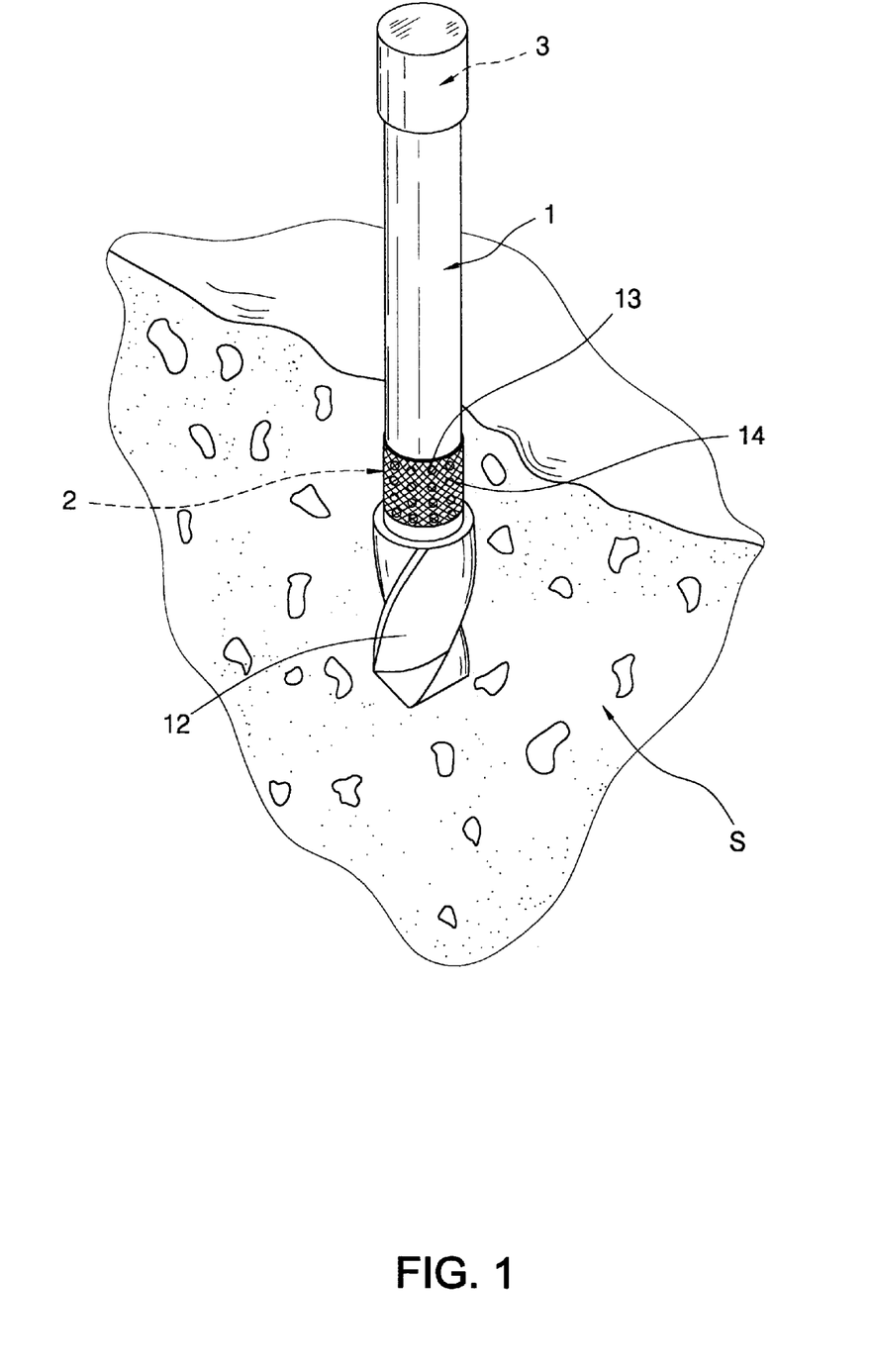
FIG. 1 is a perspective view of an apparatus for detecting saturation of water in soil according to a first embodiment of the present invention.

Referring to FIG. 1, the apparatus for detecting saturation of water in soil includes a housing 1 to be partially inserted in soil S, a sensor unit 2 received in housing 1 and a control unit 3 mounted on housing 1.

Figure 2:
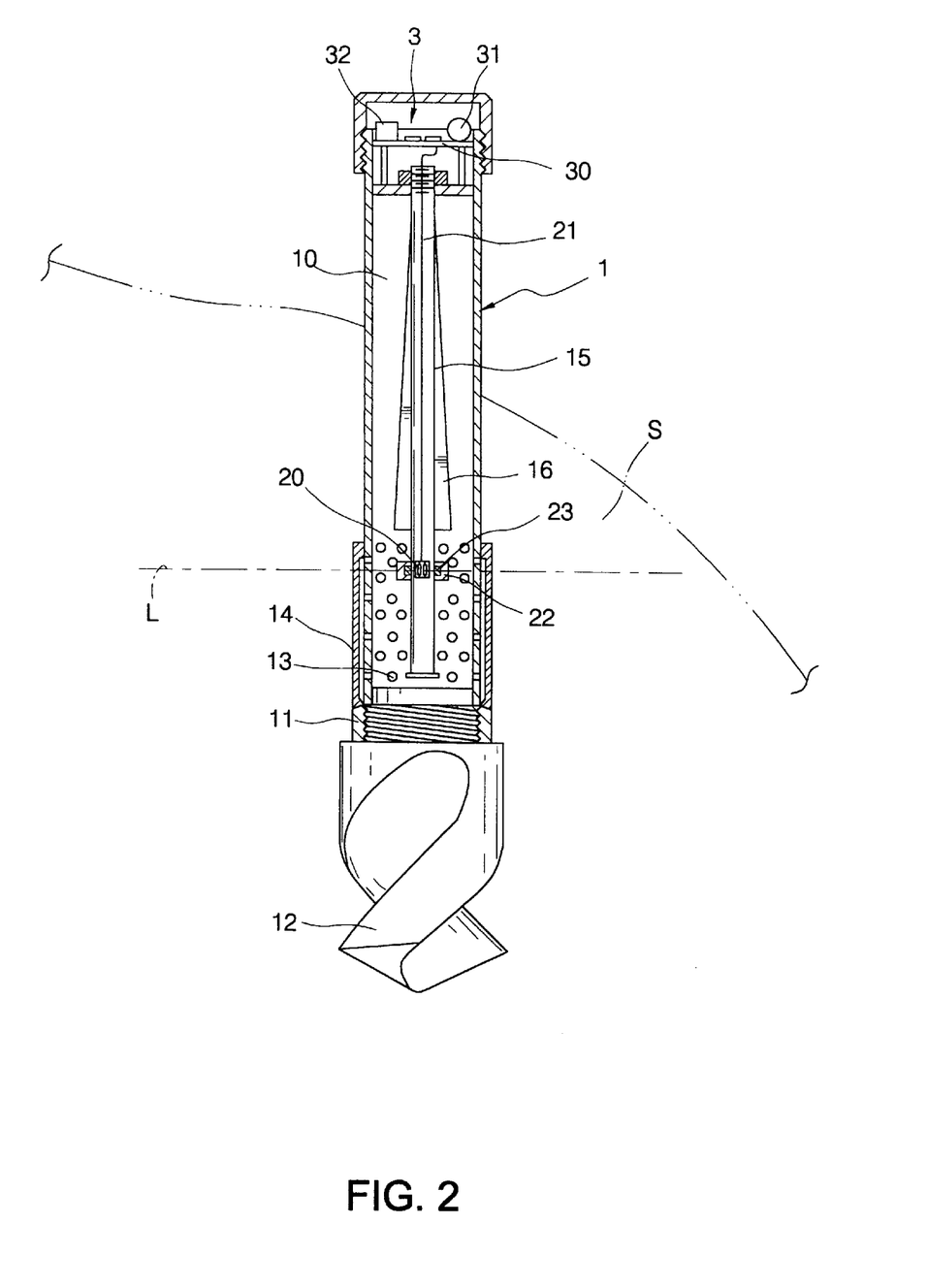
FIG. 2 is a cross-sectional view of the first embodiment shown in FIG. 1.

Housing 1 includes a lower section 11 with which a drill 12 is integrated. It is obvious that, by rotating housing 1, drill 12 can drill into soil S, thus inserting lower section 11 of housing 1 into soil S. A number of apertures 13 are defined in lower section 11 of housing 1 for permitting water into interior 10 of housing 1. A filter 14 is attached to housing 1 so as to cover apertures 13. Referring to FIG. 2, filter 14 is engaged with housing 1 by means of threads. Filter 14 may be made of non-woven cloth or any other appropriate materials that permit water while blocking soil. A guide 15 is positioned in housing 1. Guide 15 is shaped as a cylinder.

Referring to FIG. 2, sensor unit 2 includes a reed switch 20 received in guide 15. Reed switch 20 is electrically connected with control unit 3 through a pair of electric wires 21. A float 22 is shaped as a ring for collaring guide 15, thus allowing float 22 to move along guide 15. When water enters housing 1, water level L rises, thus causing float 22 to move up. A magnet 23 is attached to float 22 so that they move together with each other. When water level L reaches a pre-determined position in housing 1, magnet 23 is detected by means of reed switch 20. This is taken as that water content in soil reaches saturation. Two fins 16 are formed on or attached to guide 15. Fins 16 are used to re-enforce guide 15 on one hand and stop float 20 on the other hand.

Figure 3:
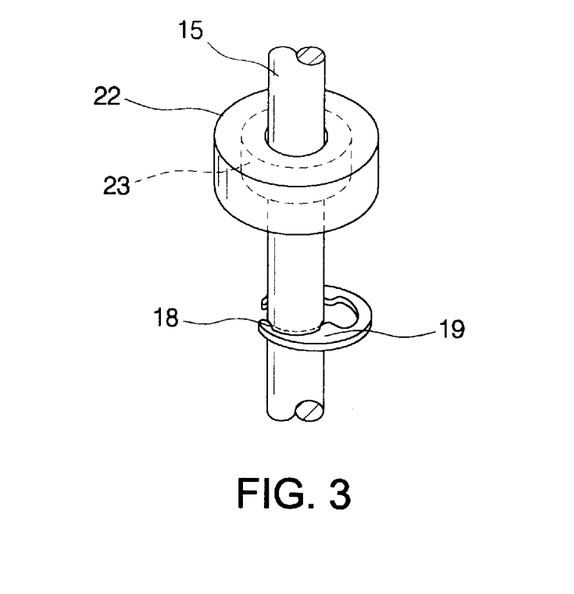
FIG. 3 is a perspective view of a sensor unit of used in the first embodiment shown in FIG. 2.

Referring to FIG. 3, guide 15 includes a neck 18 of a reduced dimension near a lower end thereof. A C-clip 19 is engaged with neck 18 after float 22 is mounted on guide 15, thus ensuring that float 22 moves along guide 15.

Control unit 3 is used to process and transfer the signal produced by means of sensor unit 2. Control unit 3 includes a circuit board 30 received in an upper section of housing 1. Circuit board 30 is kept in a stand-by position unless it is activated by means of reed switch 20 after sensing magnet 23 coming with 22. When activated, circuit board 30 processes the signal produced by means of reed switch 20.

Figure 4:
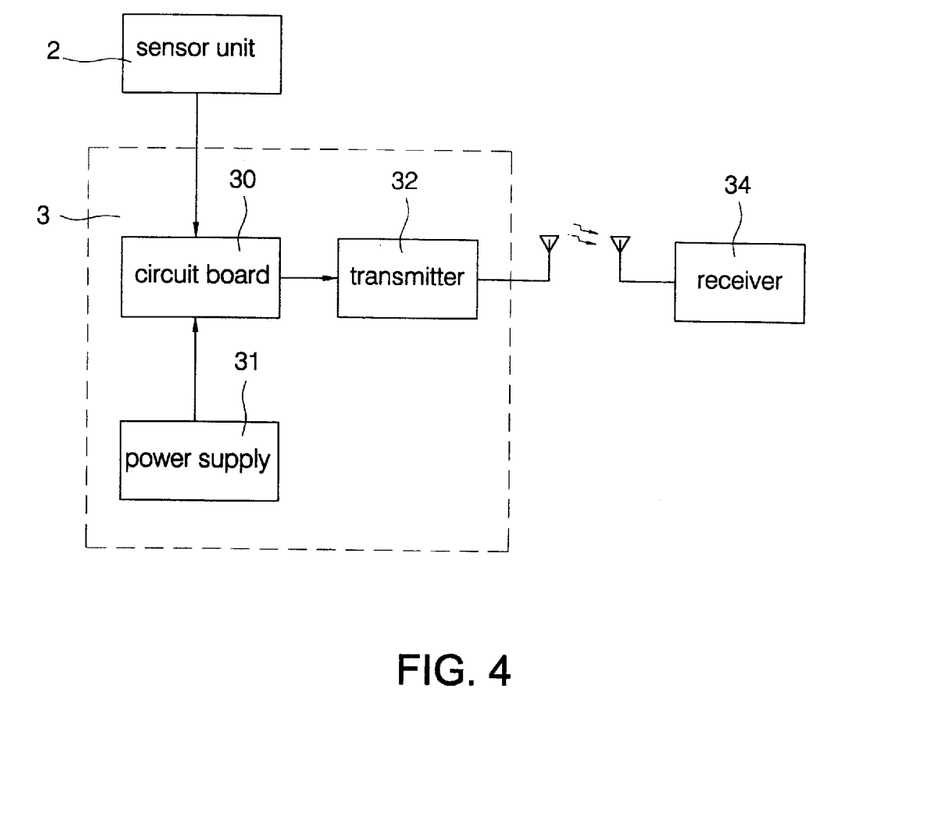
FIG. 4 is a block diagram of an electric circuit used in the apparatus for detecting saturation of water in soil according to the present invention.

Referring to FIG. 4, control unit 3 includes a wireless transmitter 32 connected with circuit board 30. Wireless transmitter 32 can transmit the signal processed by means of circuit board 30. A wireless receiver 34 is installed in a remote monitor station (not shown) in order to receive the signal from wireless transmitter 32. The received signal can be used as pre-caution so that proper operations can be performed in order to prevent heavy loss of lives and properties. Alternatively, the received signal can be used to drive proper devices to avoid heavy loss of lives and properties.

Referring to FIGS. 2 and 4, a power supply 31 is received in the upper section of housing 1, and is connected with circuit board 30 so as to provide electricity to circuit board 30. An electronic circuit is implemented in circuit board 30. The electronic circuit consumes a small amount of electricity in operation and consumes a smaller amount of electricity in the stand-by position. Therefore, power supply 31 may be a small-size battery, such as a Li cell, to provide electricity to circuit board 30 for a practically long period of time such as five years.

Figure 5:
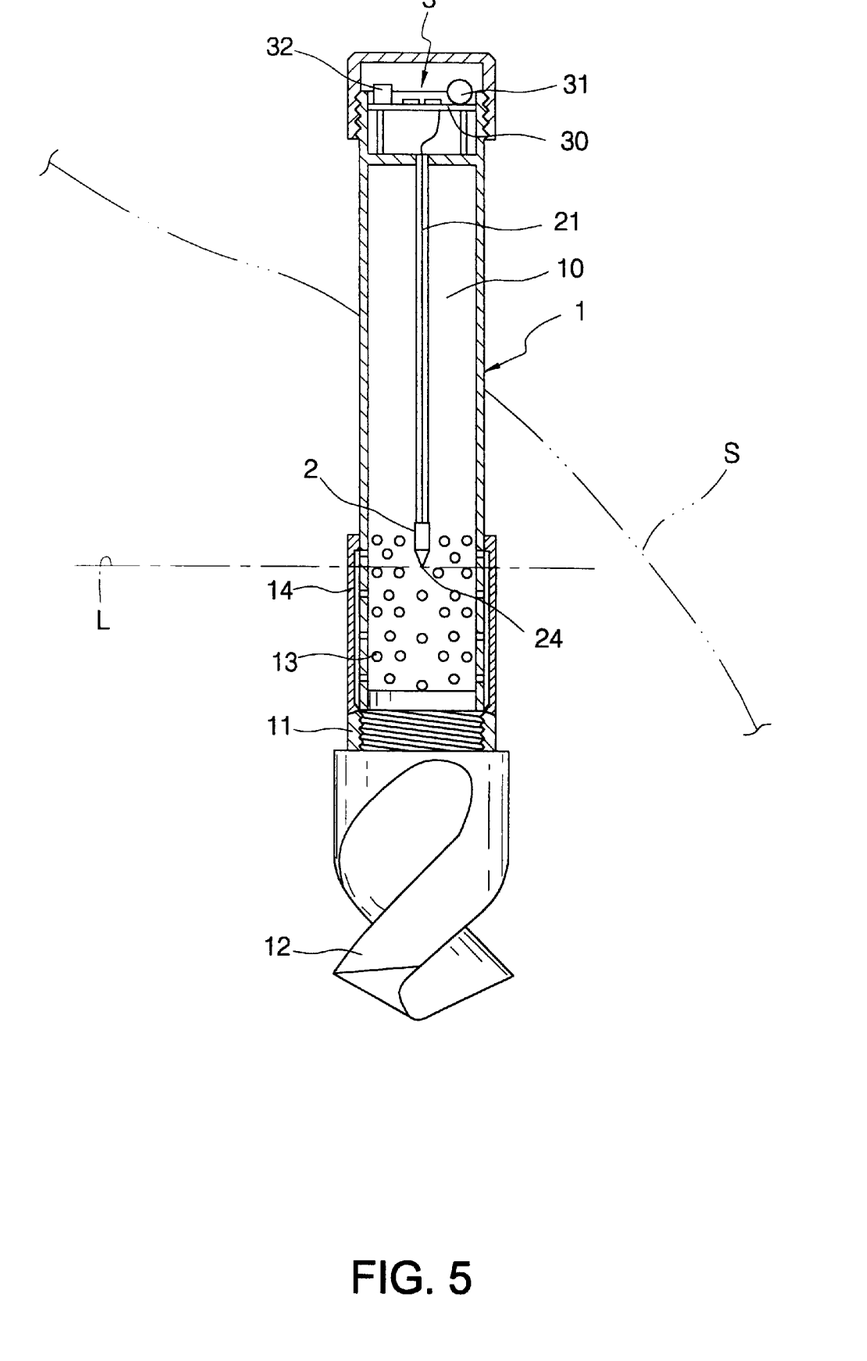
FIG. 5 is a cross-sectional view of an apparatus for detecting saturation of water in soil according to a second embodiment of the present invention.

Referring to FIG. 5, a contact switch 24 may be used to replace reed switch 20 shown in FIG. 2. Contact switch 24 includes a positive electrode and a negative electrode protruding downwards from a lower end thereof. The electrodes are separated from each other. A closed circuit will be formed when the electrodes both contact water. It is obvious that a closed circuit will be formed between the electrodes when water level L reaches the lower end of contact switch 24

Figure 6:
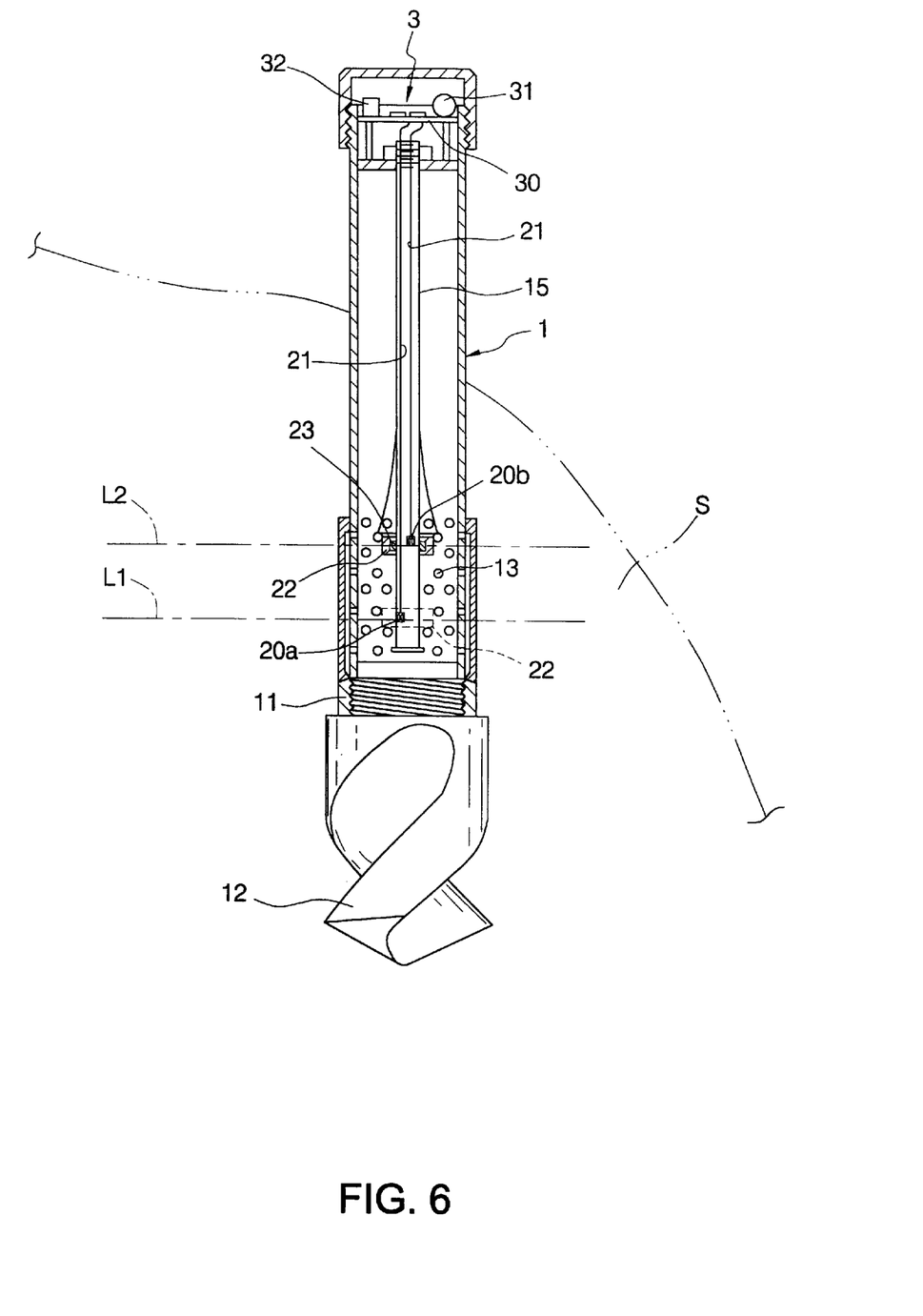
FIG. 6 is a cross-sectional view of an apparatus for detecting saturation of water in soil according to a third embodiment of the present invention.

FIG. 6 shows an embodiment identical to the embodiment of FIG. 2 except for using two reed switches instead of only one reed switch. As shown, a lower reed switch 20a indicates a lower water level L1 and an upper reed switch 20b an upper water level L2. Reed switches 20 are both electrically connected with circuit board 30 via a pair of electric wires 21. When water level L reaches L1, a signal is sent from lower reed switch 20a to circuit board 30. When water level reaches L2, a signal is sent from upper reed switch 20b to circuit board 30. A rate R at which water level L rises can be calculated by means of circuit board 30 as follows:

$$R=(L2-L1)/\Delta T$$

wherein $\Delta T$ is the time interval in which water level L rises from L1 to L2. If R reaches a pre-determined rate, it is determined that water level L rises too fast and that an alarm should be provided.

Figure 7:
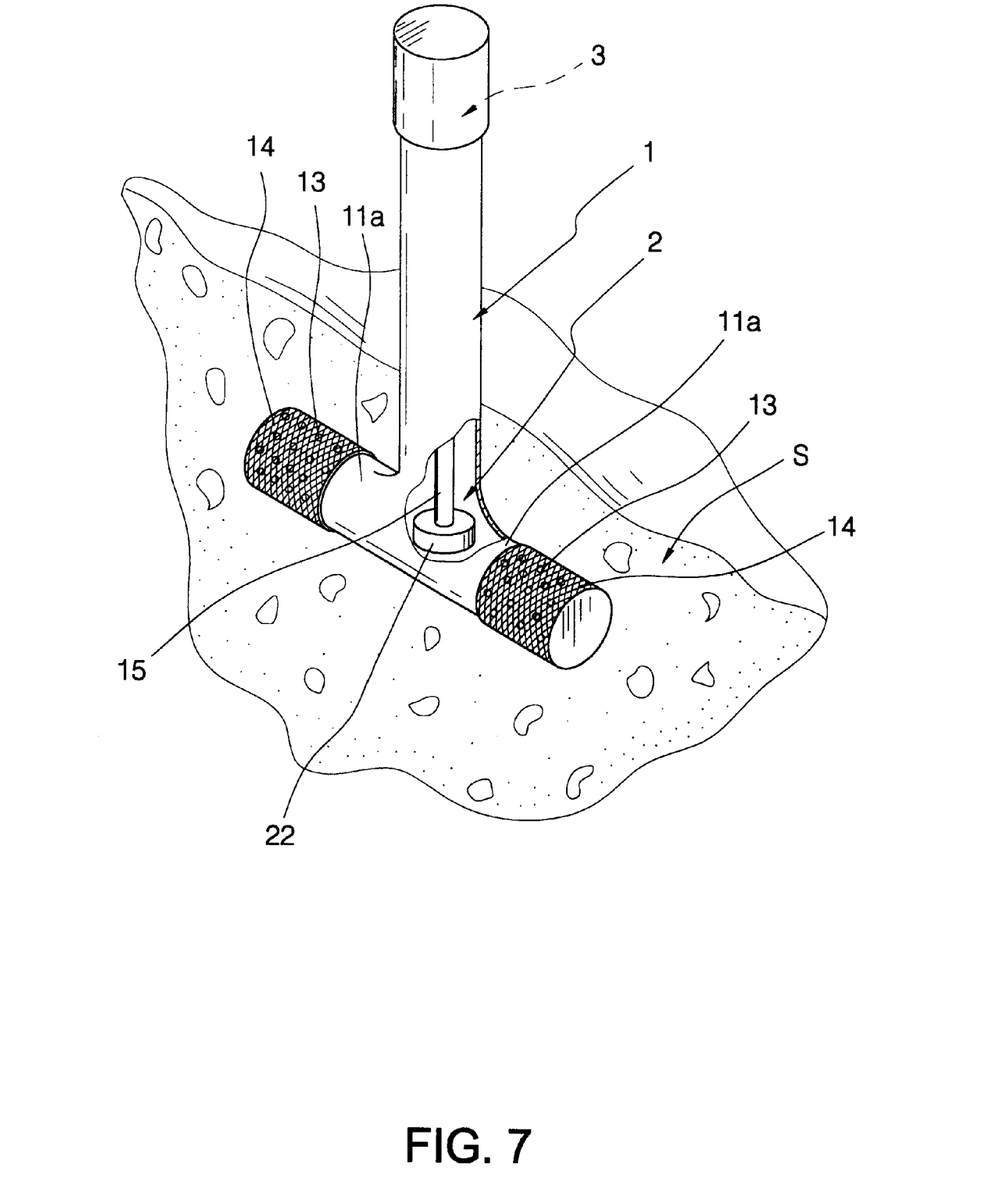
FIG. 7 is a cross-sectional view of an apparatus for detecting saturation of water in soil according to a fourth embodiment of the present invention.

Referring to FIG. 7, two extensions 11a are used to replace lower section 11 as shown in FIG. 2. Each extension 11a includes a number of apertures 13 defined therein and is covered by means of a filter 14. Obviously, soil S must be drilled or dug with a hole in order to bury extensions 11a.

Figure 8:
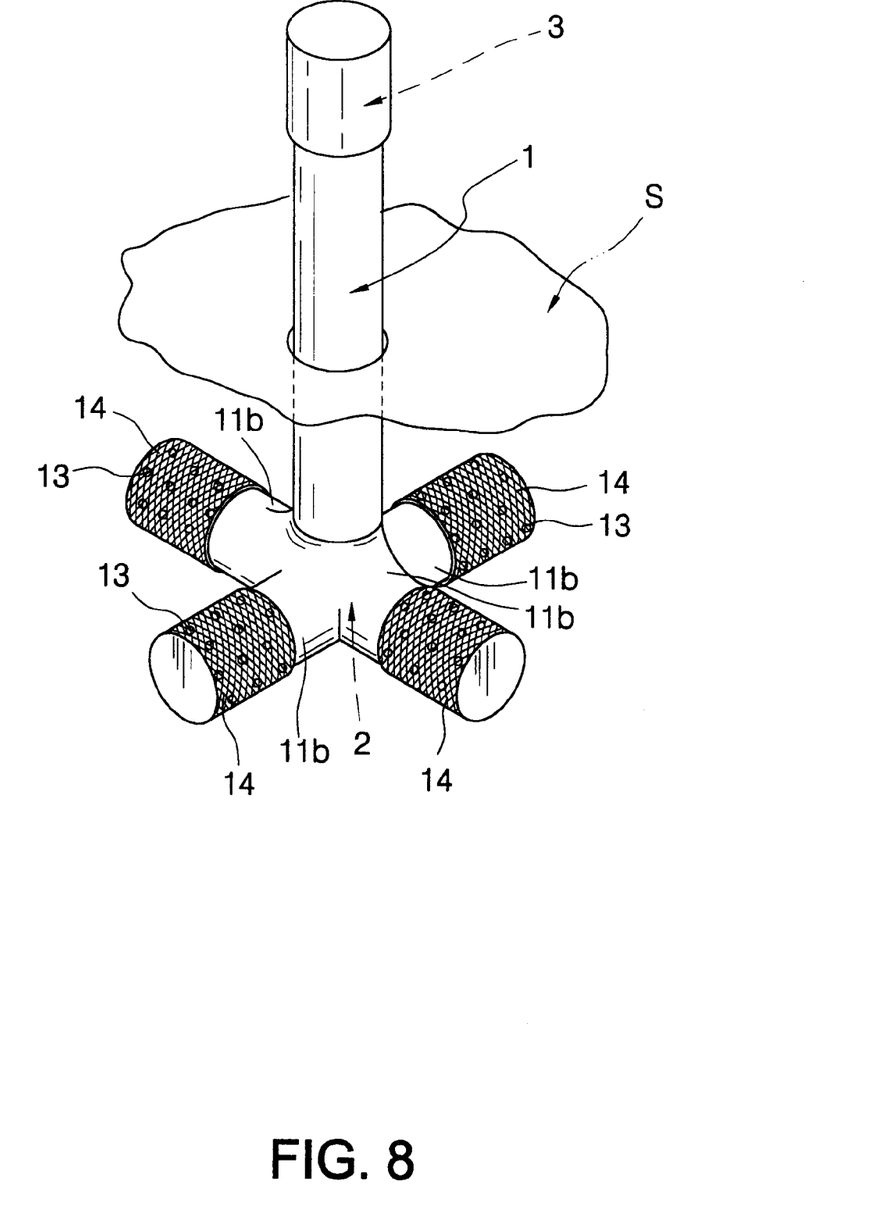
FIG. 8 is a cross-sectional view of an apparatus for detecting saturation of water in soil according to a fifth embodiment of the present invention.

Referring to FIG. 8, four extensions 11b are used to replace lower section 11 as shown in FIG. 2. Each extension 11b includes a number of apertures 13 defined therein and is covered by means of a filter 14. Obviously, soil S must be drilled or dug with a hole in order to bury extensions 11b.

The present invention has been described based on several embodiments that are illustrated for exemplary purposes and shall not be deemed to impose any limitations on the scope thereof. After a study of this specification, those skilled in the art shall be able to make variations and modifications of the described embodiments without departing the scope of the present invention.

What is claimed is:

1. An apparatus for detecting saturation of water in soil comprising:

a housing including a lower section adapted for insertion in soil;

means for permitting water into the housing while blocking soil;

a sensor unit received in the housing for sending a signal when water level reaches a predetermined position; and a control unit for receiving the signal from the sensor unit and for processing the signal, the control unit including a circuit board received in the housing and a power supply connected with the circuit board.

2. The apparatus according to claim 1 wherein the housing includes a drill protruding from the lower section thereof for drilling into soil.

3. The apparatus according to claim 1 wherein the means for permitting water into the housing while blocking soil includes a number of apertures defined in the lower section of the housing.

4. The apparatus according to claim 3 wherein the means for permitting water into the housing while blocking soil includes a filter for covering the apertures.

5. The apparatus according to claim 4 wherein the filter is made of non-woven cloth.

6. The apparatus according to claim 1 wherein the sensor unit includes:

a reed switch located in the pre-determined position;

a float for floating on the water in the housing, thus performing as an indicator of the water level; and a magnet attached to the float so that the reed switch detects the magnet and sends a signal when the water level reaches the pre-determined position.

7. The apparatus according to claim 6 including a guide received in the housing for guiding the float.

8. The apparatus according to claim 7 wherein the guide is shaped as a cylinder and the float is shaped as a ring for collaring the guide.

9. The apparatus according to claim 8 wherein the reed switch is received in the guide shaped as a cylinder.

10. The apparatus according to claim 1 wherein the sensor unit includes a contact switch located in the pre-determined position in order to send a signal when in contact with water.

11. The apparatus according to claim 10 wherein the contact switch includes positive and negative electrodes so that a closed circuit can be formed when the positive and negative electrodes both contact water.

12. The apparatus according to claim 1 wherein the control unit includes a circuit board received in an upper section of the housing and a power supply connected with the circuit board.

13. The apparatus according to claim 1 wherein the power supply is a Li cell received in the housing.

14. The apparatus according to claim 1 wherein the lower section of the housing includes a number of extensions.

* * * * *